United States Patent [19]

Sokolowski

[11] Patent Number: 5,163,557
[45] Date of Patent: Nov. 17, 1992

[54] DISPOSABLE TRAY FOR CONTRAST MEDIA MEDICAL PROCEDURES

[75] Inventor: Theresa A. Sokolowski, Mentor, Ohio

[73] Assignee: Picker International, Inc., Highland Hts., Ohio

[21] Appl. No.: 745,917

[22] Filed: Aug. 16, 1991

[51] Int. Cl.$^5$ .............. A61B 19/02; B65B 55/02
[52] U.S. Cl. .................... 206/439; 53/425; 206/370; 206/571; 422/34; 422/302
[58] Field of Search ............ 206/438, 439, 570-572, 206/363, 364, 368, 370; 422/34, 300, 302; 53/425

[56] References Cited

U.S. PATENT DOCUMENTS

| | | |
|---|---|---|
| 3,061,087 | 10/1962 | Scrivens et al. |
| 3,613,685 | 10/1971 | Reynolds. |
| 3,770,119 | 11/1973 | Hultberg et al. |
| 3,954,174 | 5/1976 | Kraus. |
| 4,195,734 | 4/1980 | Boner et al. |
| 4,482,053 | 11/1984 | Alpen et al. ............ 206/439 |
| 4,522,307 | 6/1985 | Paikoff ................. 206/570 |
| 4,523,679 | 6/1985 | Paikoff et al. .......... 206/370 |
| 4,989,733 | 2/1991 | Patry. |
| 5,014,494 | 5/1991 | George. |

FOREIGN PATENT DOCUMENTS 1192525 8/1985 Canada .................. 206/439

OTHER PUBLICATIONS

Advertisement for Picker Single-Use Trays, Trays & Disposables, Chapter 8 pp. 190-194.

Primary Examiner—Bryon P. Gehman
Attorney, Agent, or Firm—Timothy B. Gurin

[57] ABSTRACT

A unitary tray base (10) includes a first region (20) and a second region (22) which are separated by a demarcation zone (16). Medical products (30) are received in pockets (32) of the first tray region. An ethylene oxide permeable lid portion (40) seals the first tray portion from the second tray portion and the ambient atmosphere. The tray and received medical products are sterilized with ethylene oxide or other sterilizing procedures. After the sterilization, a vial (50) of contrast agent, which cannot be present during the sterilizing, is placed in a pocket (50a) of the second tray portion. A second lid portion (52) seals the vial in the second tray portion. The lid portions are marked (60-68) to indicate that the contents of the first region are sterile and the contents of the second region are not.

15 Claims, 2 Drawing Sheets

DISPOSABLE TRAY FOR CONTRAST MEDIA MEDICAL PROCEDURES

BACKGROUND OF THE INVENTION

The present invention relates to the field of medical equipment. It finds particular application in conjunction with a tray which holds both sterilized set of medical products and an unsterilized vessel of contrast media and will be described with particular reference thereto. It is to be appreciated, however, that the invention will also find application in conjunction with trays for carrying a plurality of products, a fraction of which have been treated and a fraction of which have not, such as trays for carrying medical products which have been sterilized and medical products which have not been sterilized.

Commonly, a tray holds the set of sterilized medical products, such as syringes, needles, and the like, which are used for a selected procedure. The medical products are typically sterilized by exposure to ethylene oxide gas. Contrast media that is used in various medical procedures is typically packaged in a vial that has a fixed rubber stopper through which a sterile needle is inserted to withdraw sterile contrast media. However, due to the rubber interface, the contrast media vial cannot be sterilized with ethylene oxide gas.

For medical procedures which require a contrast media, various approaches have been taken. In the first approach, a tray of sterile medical products was provided without the vial of the contrast media. The contrast media vial was provided separately. Omitting the contrast media from the tray entirely defeated the primary purpose of using disposable, prepackaged trays. That is, all products necessary for completing the single procedure were not available in a common tray base.

One technique for providing both sterile syringes and other medical products and non-sterile contrast media vials in a common tray was to provide individually wrapped, sterilized medical products. The individually wrapped medical products were then stored in a non-sterile tray with the non-sterile contrast media vial. A primary drawback to this approach was that unwrapping each of the medical products was time consuming and a nuisance to the medical personnel.

An analogous approach was to seal the contrast media in an ethylene oxide impermeable, thick metallic packaging. Only the contrast media had individual wrappings that required removal. This enabled the other medical products to be sterilized. In addition to unwrapping the individual packaging for the contrast media, it was difficult to recognize which products within the unibody tray were sterile and which were not. Moreover, while this approach worked for ethylene oxide gas sterilization, it was not effective for sterilization by radiation.

The present invention contemplates a new and improved tray design which overcomes the above-referenced problems and others.

SUMMARY OF THE INVENTION

In accordance with the present invention, a unitary tray base is provided which carries both sterilized medical products and non-sterilized medical products in clearly marked sections.

In accordance with a more limited aspect of the present invention, the non-sterile product is a vial of contrast media.

In accordance with another more limited aspect of the present invention, the medical products are held in recessed regions of the tray. The recessed regions for the sterilized and the non-sterilized products being separated by a non-recessed demarcation zone.

In accordance with another aspect of the present invention, the region of the tray which holds the sterilized products has a first sealed lid and the region with the nonsterile products has a second sealed lid.

In accordance with a more limited aspect of the present invention, the first lid is configured at least in part of an ethylene oxide permeable, pathogenic microbe impermeable barrier such that the sterile instruments can be sterilized after the first lid is sealed to the tray. A primary advantage of the present invention is that all components needed for completing the given procedure, both sterile and non-sterile, are present in a single kit.

Another advantage of the present invention is that sterile and non-sterile products are clearly denoted.

The non-sterile section cannot be confused with the sterile section. Each section is opened separately.

Still further advantages of the present invention will become apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
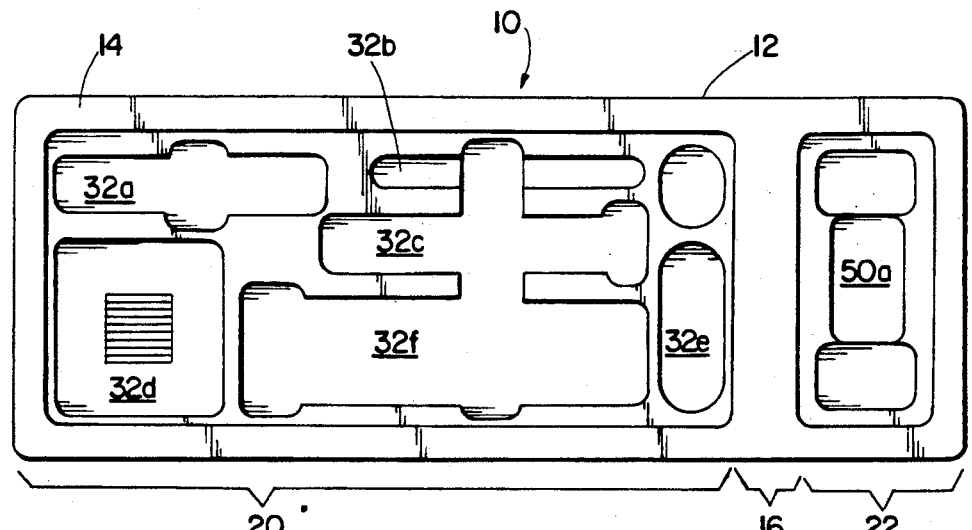
FIG. 1 is a top view of a tray base in accordance with the present invention.
Figure 2:
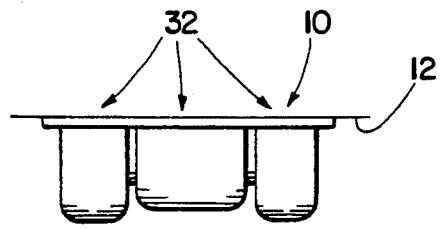
FIG. 2 is an end view of a tray base of FIG. 1.

With reference to FIGS. 1 and 2, a plastic tray base 10 is constructed as a unitary element. The tray base includes a peripheral flange 12 that defines a planar sealing surface 14 on an upper face thereof. The sealing surface further extends along a demarcation portion 16 such that a generally FIG. 8 shaped sealing plane is defined.

A first or sterile portion 20 is defined to one side of the demarcation zone 16 and a second or non-sterile portion 22 is defined to the other. Optionally, these two portions may be color coded, embossed with appropriate indicia, or the like to alert the user which side is sterile and which side is not.

Figure 3:
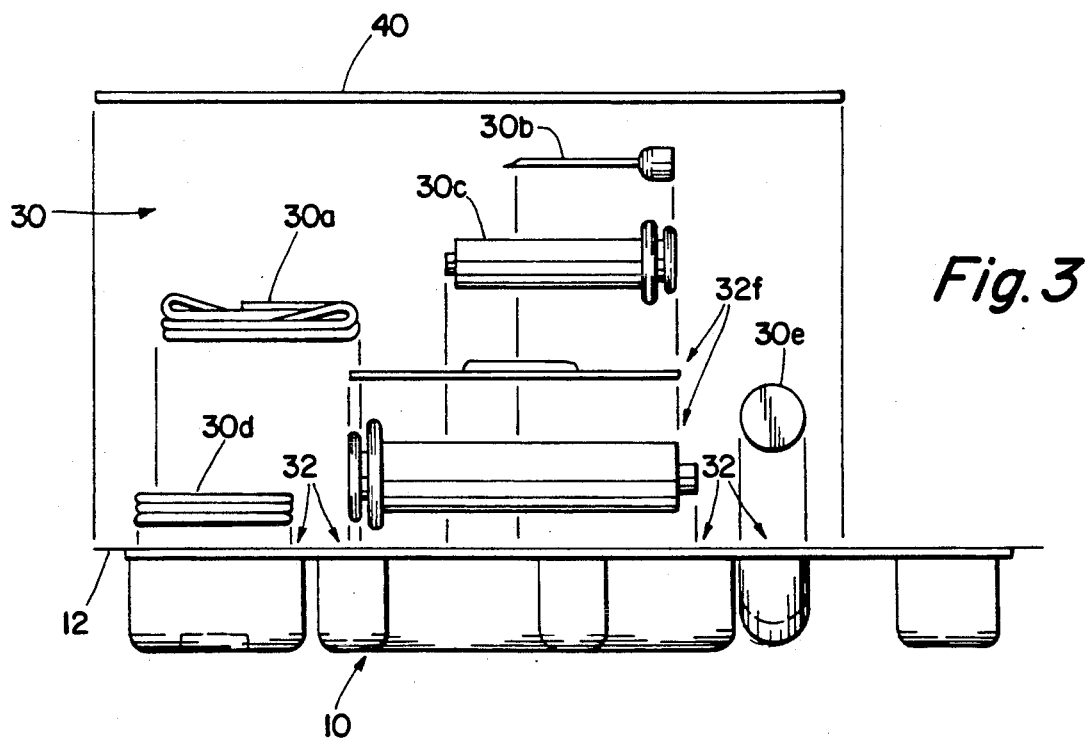
FIG. 3 is an exploded, side view of the tray base of FIG. 1, medical products to be inserted in the sterile side, and a lid.

With continuing reference to FIGS. 1 and 2 and further reference to FIG. 3, an array of medical products 30 are disposed in pockets or recesses 32 into molded the tray base 10. The exact medical products and the corresponding pockets in the tray base are determined by the procedure to which the tray is dedicated. In the illustrated embodiment, the medical products include a drain 30a, which is received in a correspondingly shaped pocket 32a, a contrast withdrawal needle 30b which is received in corresponding pocket 32b, a 5 cc syringe 30c which is received in a corresponding pocket 32c, sterile dressings 30d that are received in a corresponding pocket 32d, an ampule 30e of sodium chloride solution that is received in a pocket 32e, and other medical products 32f such as a sodium chloride insert, band aid, 20 cc syringe, and examination gloves that are received in a corresponding pocket 32f. Other combinations of products and pockets as are appropriate to other procedures are contemplated.

A first lid portion 40 is sealed to the first portion of the sealing surface 14 of the tray base that surrounds the first tray portion 20 to seal the first tray portion from the second tray portion and the ambient atmosphere. The first lid portion 40 is constructed at least in part of ethylene oxide permeable material that has pores sufficiently small or torturous that pathogenic microorganisms are prevented from passing therethrough. In the preferred embodiment, the first lid 40 is constructed of a spunbonded polymer filter such as TYVEK TM (a trademark of E. I. DuPont de Nemours) spunbonded olefin material. The spunbonded fibers define small tortuous voids which allow the ethylene oxide to pass but are too small or tortuous for blocking the passage of bacteria and other pathogenic microbes to pass. Because airborne microorganisms are dependent on air currents for movement, tortuous paths are effective to prevent their entry. Once the sterile side lid portion 40 is sealed to the tray base, the entire assembly, including the tray, lid, and medical products, is sterilized using ethylene oxide or other known sterilizing techniques.

Figure 4:
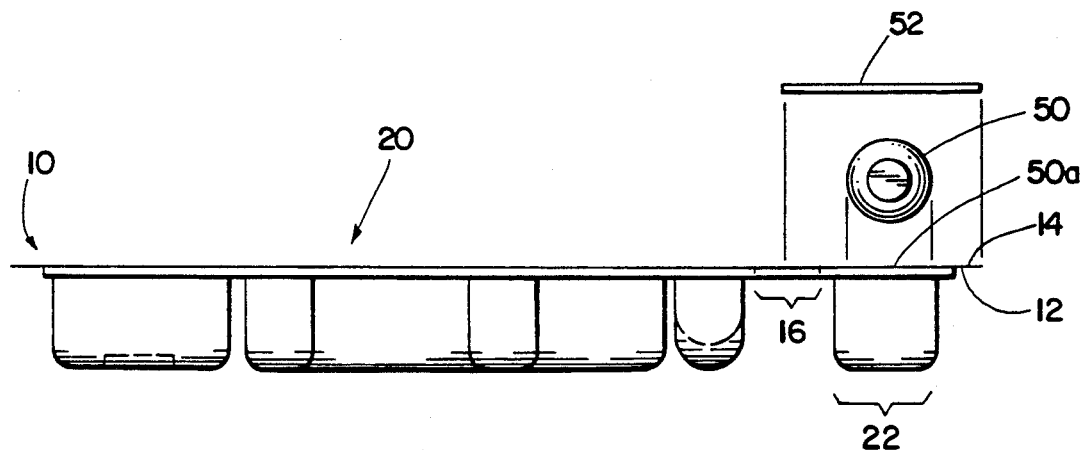
FIG. 4 is a an exploded, side view of the tray base with the lid of FIG. 3 sealing the medical products into a sterile side thereof, a vial of contrast agent, and a lid for the non-sterile side.

With reference to FIG. 4, after the tray base and medical products sealed into the sterile side 20 have been sterilized, a vial 50 of contrast agent is inserted into a matching recess 50a on the non-sterile side of the tray base. The contrast agent and the interior of the vial are normally sterilized at the time of packaging. The vial is closed with a cannula penetrable closure, such as a rubber member which is degraded by ethylene oxide sterilization. The exterior of the vial becomes non-sterile from subsequent handling. A second lid portion 52 is sealed to the second portion of the sealing surface 14 surrounding the second tray portion. In the preferred embodiment, the non-sterile lid portion 52 is also the spunbonded material. In this manner, the lids for both the sterile and non-sterile sides are removed with analogous force and convenience. Optionally, other materials may be used for the second lid portion on the non-sterile side. In an alternate embodiment, the non-sterile lid 52 includes an ethylene oxide impermeable foil layer which is sealed with an ethylene oxide impermeable seal to the sealing region 26 of the tray base. This permits the contrast agent to be sealed into the tray base before the ethylene oxide sterilizing step.

Figure 5:
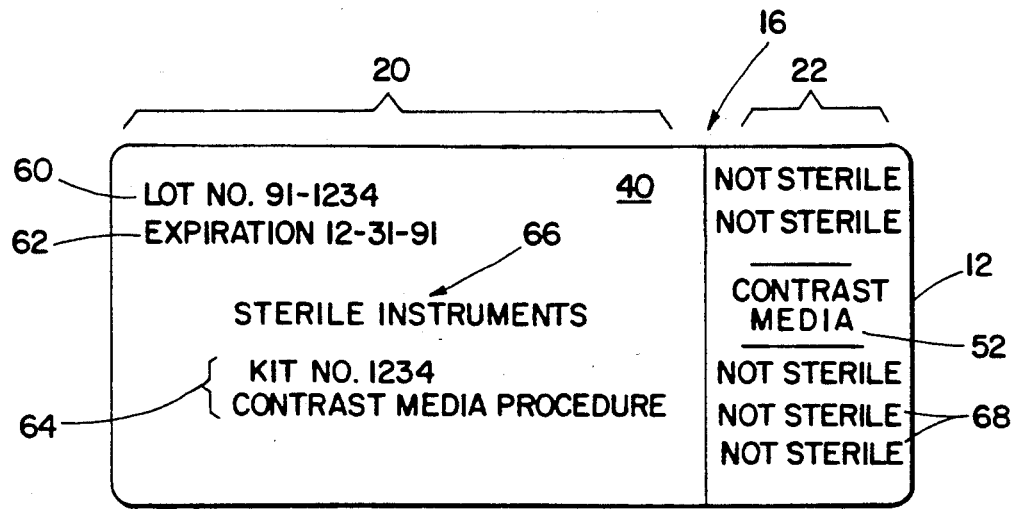
FIG. 5 is a top view of the assembled kit with the lids sealed to the sterile and non-sterile sides.

With reference to FIG. 5, the sterile side lid portion 40 is marked with appropriate indicia, for example, a sterilization lot number 60, an expiration date 62, an identification of the kit or medical procedure 64, the notation "sterile" 66, or the like. The non-sterile side lid portion 52 is clearly and boldly marked with indicia 68 which indicate that the compartment under lid portion 52 is not sterile. Various words, color coding, graphic or pictorial images, and the like may be provided.

The invention has been described with references to the preferred embodiment. Obviously, modifications and alterations will occur to others upon reading and understanding the preceding detailed description. It is intended that the invention be construed as including all such alterations and modifications insofar as they come within the scope of the appended claims or the equivalent thereof.

Having thus described the preferred embodiment, the invention is now claimed to be:

1. A tray assembly for holding a set of medical products for use in a selected procedure, the assembly comprising:

a one-piece tray base, the tray base defining a sterile region, a non-sterile region, and a demarcation zone between the regions, the tray base defining a sealing surface with a sealing surface portion peripherally around each of the sterile and non-sterile regions, each sealing surface portion including part of the demarcation zone;

the tray base sterile region defining a plurality of medical product-receiving pockets, each pocket having an internal bottom, within which the set of medical products for use in the selected procedure are contained;

the tray base non-sterile region defining a pocket having an integral bottom in which a vial of contrast agent which is unsuited to sterilization is contained;

a first lid portion sealed to the sealing surface portion around the tray base sterile region, the first lid portion being impermeable to pathogenic microorganisms, whereby pathogenic microorganisms are blocked from contaminating the sterile region, the medical products, and an interior of the first lid portion, the first lid portion including at least a portion which is permeable to gaseous sterilants, whereby the medical products, the sterile region, and the interior of the first lid portion are sterilizable after the first lid portion is sealed to the tray;

a second lid portion sealed to the sealing surface portion around the non-sterile tray base region;

wherein either one of the sealed sterile region and sealed non-sterile region can be separately opened without affecting the seal integrity of the other sealed region.

2. The assembly as set forth in claim 1 further including indicia on at least one of the lid portions for denoting the sterile and non-sterile tray base regions.

3. The assembly as set forth in claim 2 wherein the indicia includes:

a sterilization lot number and expiration date on the first lid portion;

a designation of a non-sterile condition on the second lid portion.

4. The assembly as set forth in claim 1 wherein the vial is sealed with a cannula-permeable rubber closure which rubber closure is unacceptably degraded by ethylene oxide sterilization.

5. The assembly as set forth in claim 4 wherein the set of medical products sealed in the sterile region of the tray base includes a syringe, needle, and bandaging materials.

6. The assembly as set forth in claim 5 wherein the tray base portion includes a pocket for each medical product of the medical product set, each pocket conforming closely to a peripheral shape of the corresponding medical product, each pocket including an expanded portion to facilitate manual access to the received medical product.

7. The assembly as set forth in claim 1 wherein the first lid portion includes a spunbonded polymeric filter material which defines paths therethrough which permit passage of ethylene oxide sterilization gas and which paths are too narrow and tortuous for pathogenic microorganisms to pass.

8. The assembly as set forth in claim 7 wherein the second lid portion includes spunbonded polymeric material, such that the first and second lid portions are removable with substantially the same force and convenience.

9. A tray assembly comprising:
a tray base which defines a first region and a second region, the first and second regions each defining at least one product-receiving pocket therein, each pocket having an integral bottom;
a first set of products contained in the pockets of the first tray region;
a first lid portion sealed to the tray base and covering the first tray region only such the first lid portion seals the first tray region from the second tray region and the ambient atmosphere, the products of the first tray region being sterilized after attachment of the first lid portion;
a product which is degraded by the sterilization process contained in one pocket of the second tray region;
a second lid portion sealed to the tray base and covering the second tray region only sealing the second tray region from the first tray region and the ambient atmosphere;
wherein either one of the first and second lid portions is removable without affecting the seal integrity of the other lid portion.

10. The assembly as set forth in claim 9 wherein the product contained in the second tray region includes a container of a drug whose stability is not maintained during sterilization.

11. The assembly as set forth in claim 10 wherein the product contained in the second tray region includes a contrast agent.

12. The assembly as set forth in claim 11 wherein the first set of products includes medical instruments including a needle and syringe for injecting the contrast agent.

13. The assembly as set forth in claim 10 wherein the first lid portion includes a porous spunbonded material such that the first set of products and the first tray region can be sterilized by ethylene oxide gas through the first lid portion.

14. The assembly as set forth in claim 10 wherein the first lid portion bears an indicia indicative of the sterilization procedure and an expiration date and wherein the second lid portion includes an indicia that the second tray region and at least the exterior surface of the contained product have not been sterilized.

15. A method of packaging a set of medical products for a selected medical procedure, the method comprising:
forming a one-piece tray base having a first region including a plurality of medical product receiving pockets with integral bottoms, a second region defining a contrast agent vial-receiving pocket with an integral bottom, and a demarcation zone between the regions, the tray base defining a sealing surface portion peripherally around each of the first and second regions, each sealing surface portion including part of the demarcation zone;
placing the set of medical products in the pockets of the first tray region;
sealing a first lid portion to the sealing surface portion around the first tray region such that the first tray region is sealed from the second tray region and the ambient atmosphere, the first lid portion blocking microorganisms from passing therethrough and being permeable to sterilant gases;
sterilizing the tray base, the first lid portion, and the medical products sealed in the first tray region with a sterilant gas;
placing a vial of contrast agent in the contrast agent vial-receiving pocket of the second tray region;
sealing a second lid portion to the sealing surface portion around the second tray region;
wherein either one of the first and second lid portions is removable without affecting the seal integrity of the other lid portion.

* * * * *